(12) United States Patent
Takeuchi et al.

(10) Patent No.: US 7,462,696 B2
(45) Date of Patent: Dec. 9, 2008

(54) HUMAN ANTIBODIES THAT HAVE MN BINDING AND CELL ADHESION-NEUTRALIZING ACTIVITY

(75) Inventors: Toshihiko Takeuchi, Oakland, CA (US); Nathalie Dubois-Stringfellow, Berkeley, CA (US); John E. Murphy, Oakland, CA (US); Julie Rinkenberger, Moraga, CA (US)

(73) Assignee: Bayer Pharmaceutical Corporation, West Haven, CT (US)

( * ) Notice: Subject to any disclaimer, the term of this patent is extended or adjusted under 35 U.S.C. 154(b) by 111 days.

(21) Appl. No.: 10/273,541

(22) Filed: Oct. 18, 2002

(65) Prior Publication Data

US 2003/0077277 A1    Apr. 24, 2003

Related U.S. Application Data

(60) Provisional application No. 60/343,657, filed on Oct. 18, 2001, provisional application No. 60/377,716, filed on May 2, 2002.

(51) Int. Cl.
*C07K 16/46* (2006.01)
*C07K 16/24* (2006.01)

(52) U.S. Cl. .............. 530/387.3; 530/388.23; 530/388.7

(58) Field of Classification Search .............. 424/155.1, 424/133.1; 530/388.8, 388.85, 389.7
See application file for complete search history.

(56) References Cited

U.S. PATENT DOCUMENTS 6,297,051 B1 * 10/2001 Zavada et al. ................ 435/375
6,632,927 B2 * 10/2003 Adair et al. .............. 530/387.3
6,689,744 B2 * 2/2004 Gao et al. ...................... 514/2

OTHER PUBLICATIONS

Panka et al. Variable region framework differences result in decreased or increased affinity of variant anti-digoxin antibodies. Proc Natl Acad Sci U S A. 85(9):3080-3084, 1988.*
Rudikoff et al Single amino acid substitution altering antigen-binding specificity. Proc Natl Acad Sci U S A. Mar. 1982 79(6): 1979-83.*
Pastorek, J. et al, *Oncogene*(1994), 9, 2877-2888).
Liao, S.Y., et al, *Am J Pathol*(1994), 145, 598-609).
Liao, S.Y., *Cancer Res*(1997) 57, 2827-2831).
Turner, J.R. *Hum Pathol*, (1997) 28, 740-744).
Saarnio, J. et al, *Am J Pathol*(1998) 153, 279-285).
Vermylen, P. et al, *Eur Respir J*(1999), 14, 806-811).
Chia, S. K. et al, *J. Clin. Oncol.* (2001) 19, 3660-3668).
Knappik, et al., "Fully Synthetic Human Combinatorial Antibody Libraries (HuCAL) Based on Modular consensus Frameworks and CDRs Randomized with Trinucleotides," *J. Mol. Biol.*,296: 57-86 (2000).
Xu, et al., "Diversity in the CDR3 Region of $V_H$ is Sufficient for Most Antibody Specificities," *Immunity*, 13: 37-45 (2000).

* cited by examiner

*Primary Examiner*—Maher M Haddad
(74) *Attorney, Agent, or Firm*—Edwards Angell Palmer & Dodge LLP; Barry Kramer; Ralph Loren

(57) ABSTRACT

The invention is composed of monoclonal human MN antibodies or MN antibody fragments that target the GEEDLP (SEQ ID NO: 118) repeat within the proteoglycan domain. The proteoglycan domain of the MN cell surface protein contains four of these identical GEEDLP (SEQ ID NO: 118) repeats. Binding to the desired epitope is verified by competition ELISA, where ELISA signal can be attenuated by co-incubation with a peptide containing this repeat (PGEEDLP-GEEDLP (SEQ ID NO: 119)). This inhibition of binding can also be verified using Biacore assays, where binding of desired antibodies to immobilized MN or proteoglycan peptides can be inhibited by the peptide repeat. In addition to binding to the peptide repeat, human anti-MN antibodies can inhibit the cell adhesion of CGL-1 cells to MN coated plastic plates. Human anti-MN antibodies have been used to diagnose and quantify MN expression in cancer cells and tumors using FACS and immunohistochemical methods. An example is also provided where a human anti-MN IgG1 mediates tumor cell lysis though antibody-dependent cell-mediated cytotoxicity. Therefore, these antibodies will be useful for the treatment of cancers in which MN is upregulated or can be useful for the diagnosis of cancers in which MN is upregulated.

10 Claims, 8 Drawing Sheets

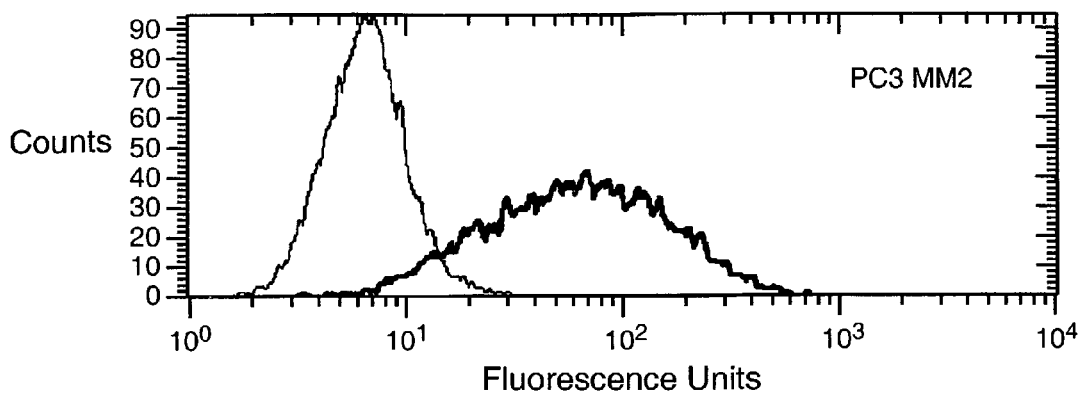

FIG._1

Sequence Information

| SEQ I.D.# | Sequence Information | DNA Sequence |
|---|---|---|
| | VH3-CDR1 | |
| 1 | 1 | GGATTTACCTTTAGCGAGAGGGCCATGACC |
| 2 | 2 | GGATTTACCTTTAGCGCGGCCATGATGACG |
| 3 | 3 | GGATTTACCTTTAGCGGGAGCATGATGGCC |
| 4 | 4 | GGATTTACCTTTAGCGACTGGGCGATGACG |
| 5 | 5 | GGATTTACCTTTGTGAAGAGCATGGTGGTG |
| 6 | 6 | GGATTTACCTTTAGCAGGAACCTGATGACC |
| 7 | 7 | GGATTTACCTTTGAGCGGTGGATGGGGGCG |
| 8 | 8 | GGATTTACCTTTAGCAGGAGGATGATGGTC |
| 9 | 9 | GGATTTACCTTTAGCAGGTGGATGATGGTC |
| 10 | 10 | GGATTTACCTTTAGCGAGAGCATGATGACG |
| 11 | 11 | GGATTTACCTTTAGCTGGCACATGATGACG |
| 12 | 12 | GGATTTACCTTTAGCTCCGTGATGATGACG |
| 13 | 13 | GGATTTACCTTTAGCGGGAGCATGATGACG |
| | VH3-CDR3 | |
| 14 | 1 | TCTGCTACTCGTTTTGATTAT |
| 15 | 2 | AATGGTACTCGTATGGATGTT |
| 16 | 3 | GGTATTGTTCGTGGTATGGATCAT |
| 17 | 4 | GGTGGTTCTCGTTATGATGTT |
| 18 | 5 | AATATTACTAAGTCTGATGTT |
| 19 | 6 | GGTGGTACTCGTTTTGATTAT |
| 20 | 7 | AATGGTCGTAATCTTGATTAT |
| 21 | 8 | ACTGCTACTCGTTTTGATTAT |
| 22 | 9 | AAGCCTTTTACTGGTAAGTATTGGGGTCATACTGGTTTTGATATT |
| 23 | 10 | AAACCTTTTACTGGTAAGTATTGGGGTCATACTGGTTTTGATATT |
| 24 | 11 | AATGGCCTGCGTATGGATGTT |

FIG._2A

Sequence Information

| SEQ I.D.# | Sequence Information | DNA Sequence |
|---|---|---|
| 25 | 12 | AATCTGCTGCGTATGGATGTT |
| 26 | 13 | AATGCGGTGCGTATGGATGTT |
| 27 | 14 | AATGCGATGCGTATGGATGTT |
| 28 | 15 | AATGCCCTCCGTATGGATGTT |
| 29 | 16 | AATGTGCTGCGTATGGATGTT |
| 30 | 17 | GGGGGGACGCGTATGGATGTT |
| 31 | 18 | CAGGGCACCCGTATGGATGTT |
| 32 | 19 | AATGGCGTGCGTATGGATGTT |
| 33 | 20 | AATGGCATCCGTATGGATGTT |
| | VL1-CDR3 | |
| 34 | 1 | CAGAGCCGTGACTATGAGAAGCCTATGATT |
| 35 | 2 | CAGAGCCGAGACTATGAGAAGCCTATGATT |
| 36 | 3 | CAGAGCCGCGACTATGAGAAGCCTATGATT |
| | VL2-CDR1 | |
| 37 | 1 | ACGGGTACTAGCAGCGATAGGACGCGCCCCGCCGAAGTACGCC |
| 38 | 2 | ACGGGTACTAGCAGCGATGTGTCCGGCCTCAACATCGTGTCC |
| | VL2-CDR3 | |
| 39 | 1 | CAGAGCTATGACCGTGCTTTTAAGTCTGTT |
| 40 | 2 | CAGAGCTATGACCATAAGAAGACTGAG |
| 41 | 3 | CAGAGCTATGACATGTTTGCTCGTGTTATT |
| 42 | 4 | CAGAGCTATGACCGTCTTTATAAGAAGCTT |
| 43 | 5 | CAGAGCTATGACCGGGCTTATCGACTTCTT |
| 44 | 6 | CAGAGCTATGACCGTTCTCGTTATGCT |
| 45 | proteoglycan A | GEEDLPSEEDSPREEDPPGEEDLPGEEDLP |
| 46 | proteoglycan B | PGEEDLPGEEDLP |
| 47 | proteoglycan C | PSEEDSPREEDP |
| | VH3-CDR1 | |
| 48 | 1 | GFTFSERAMT |
| 49 | 2 | GFTFSAAMMT |
| 50 | 3 | GFTFSGSMMA |
| 51 | 4 | GFTFSDWAMT |
| 52 | 5 | GFTFVKSMVV |
| 53 | 6 | GFTFSRNLMT |
| 54 | 7 | GFTFERWMGA |
| 55 | 8 | GFTFSRRMMV |
| 56 | 9 | GFTFSRWMMV |
| 57 | 10 | GFTFSESMMT |
| 58 | 11 | GFTFSWHMMT |
| 59 | 12 | GFTFSSVMMT |

*FIG. 2B*

Sequence Information

| SEQ I.D.# | Sequence Information | DNA Sequence |
|---|---|---|
| 60 | 13 | GFTFSGSMMT |
| | VH3-CDR3 | Amino Acid Sequence |
| 61 | 1 | SATRFDY |
| 62 | 2 | NGTRMDV |
| 63 | 3 | GIVRGMDH |
| 64 | 4 | GGSRYDV |
| 65 | 5 | NITKSDV |
| 66 | 6 | GGTRFDY |
| 67 | 7 | NGRNLDY |
| 68 | 8 | TATRFDY |
| 69 | 9 | KPFTGKYWGHTGFDI |
| 70 | 10 | KPFTGKYWGHTGFDI |
| 71 | 11 | NGLRMDV |
| 72 | 12 | NLLRMDV |
| 73 | 13 | NAVRMDV |
| 74 | 14 | NAMRMDV |
| 75 | 15 | NALRMDV |
| 76 | 16 | NVLRMDV |
| 77 | 17 | GGTRMDV |
| 78 | 18 | QGTRMDV |
| 79 | 19 | NGVRMDV |
| 80 | 20 | NGIRMDV |
| | VL1-CDR3 | |
| 81 | 1 | QSRDYEKPMI |
| | VL2-CDR1 | |
| 82 | 1 | TGTSSDRTRPPKYA |
| 83 | 2 | TGTSSDVSGLNIVS |
| | VL2-CDR3 | |
| 84 | 1 | QSYDRAFKSV |
| 85 | 2 | QSYGHKKTE |
| 86 | 3 | QSYDMFARVI |
| 87 | 4 | QSYDRLYKKL |
| 88 | 5 | QSYDRAYRLL |
| 89 | 6 | QSYDRSRYA |

FIG._2C

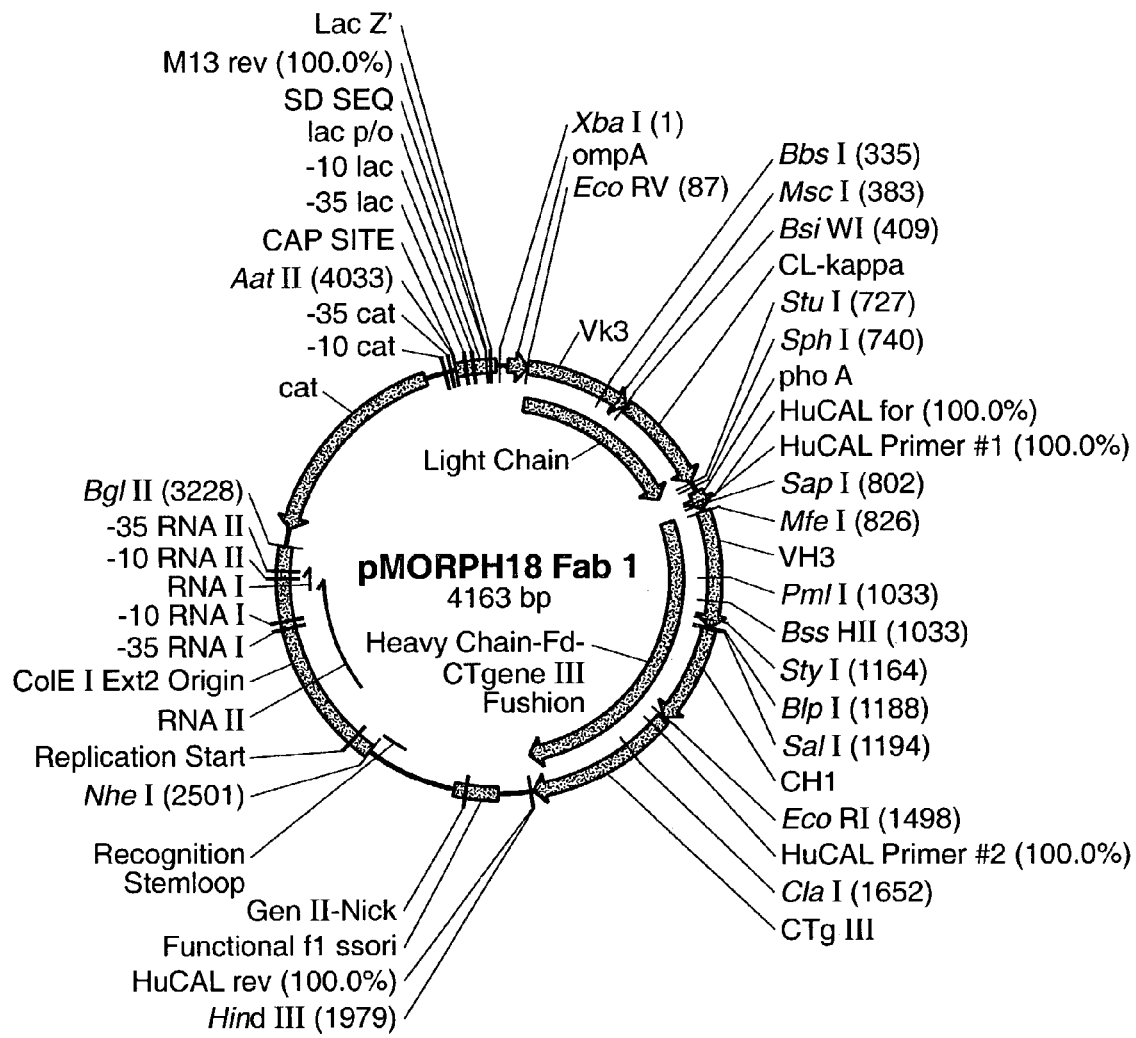
FIG._3

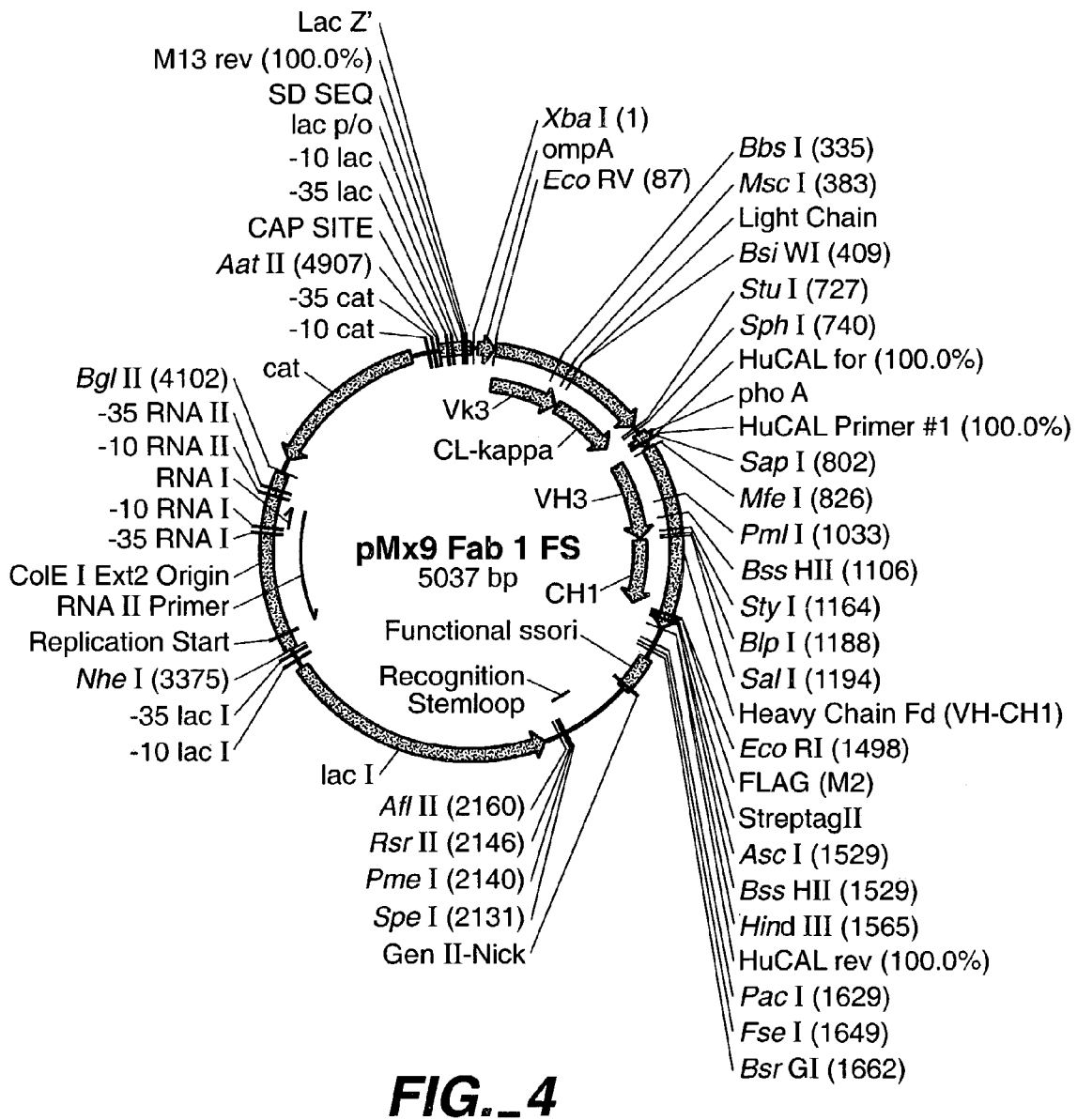
FIG._4

Blocking of Cell Adhesion with Anti-MN Antibody MN-3
20 ug / mL Ab MN-3
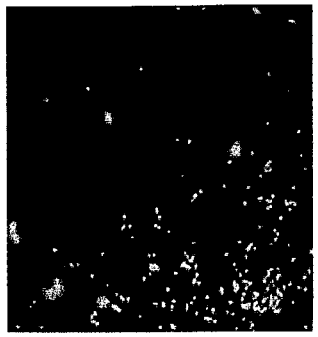
FIG._5A
Blocking of Cell Adhesion with Anti-MN Antibody MN-3
20 ug / mL Human Gamma Globulin
FIG._5B
Blocking of Cell Adhesion with Anti-MN Antibody MN-3
No Antibody Treatment
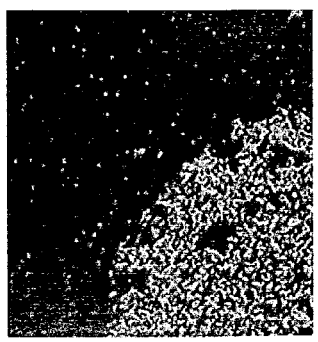
FIG._5C

Heavy / Light Chain Pairs

| Antibody | Heavy Chain / Light Chain | Approximate Affinity in BIAcore to Human MN Proteoglycan Peptide Labeled BSA | Inhibition of ELISA Signal with Proteoglycan Peptide B (1mg / ml) | Inhibition in MN Cell Binding Assay (100 ug / ml Fab) |
|---|---|---|---|---|
| 1 | VH3-CDR3-1/VL2-CDR3-1 | 1.82E-06 | 75.00% | >95% |
| 2 | VH3-CDR3-2/VL2-CDR3-4 | 3.96E-08 | 93.00% | >95% |
| 3 | VH3-CDR3-3/VL2-CDR3-6 | 4.65E-09 | 74.00% | >95% |
| 4 | VH3-CDR3-4/VL2-CDR3-1 | 6.40E-06 | 75.00% | ND |
| 5 | VH3-CDR3-5/VL2-CDR3-1 | 8.56E-07 | 32.00% | ND |
| 6 | VH3-CDR3-6/VL2-CDR3-2 | ND | 40.00% | ND |
| 7 | VH3-CDR3-7/VL2-CDR3-5 | ND | 51.00% | ND |
| 8 | VH3-CDR3-1/VL1-CDR3-1 | ND | 73.00% | ND |
| 9 | VH3-CDR3-9/VL1-CDR3-1 | ND | ND | ND |
| 10 | VH3-CDR3-9/VL1-CDR3-2 | ND | ND | ND |
| 11 | VH3-CDR3-9/VL1-CDR3-3 | ND | ND | ND |
| 12 | VH3-CDR3-10/VL1-CDR3-1 | ND | ND | ND |
| 13 | VH3-CDR3-1/VL2-CDR3-3 | 6.03E-08 | ND | ND |
| 14 | VH3-CDR3-1/VL2-CDR3-2 | ND | ND | ND |
| 15 | VH3-CDR3-1/VL2-CDR3-4 | 9.00E-08 | ND | ND |
| 16 | VH3-CDR3-1/VL2-CDR3-5 | 9.90E-08 | ND | ND |
| 17 | VH3-CDR3-1/VL2-CDR3-6 | ND | ND | ND |
| 18 | VH3-CDR3-3/VL2-CDR3-3 | ND | ND | ND |
| 19 | VH3-CDR3-3/VL2-CDR3-2 | ND | ND | ND |
| 20 | VH3-CDR3-3/VL2-CDR3-4 | ND | ND | ND |
| 21 | VH3-CDR3-3/VL2-CDR3-5 | ND | ND | ND |
| 22 | VH3-CDR3-3/VL2-CDR3-1 | ND | ND | ND |
| | ND = not determined | | | |
| 23 | VH3-CDR1-1/VH3-CDR3-1/VL2-CDR3-3 | 5.84E-09 | ND | ND |
| 24 | VH3-CDR1-2/VH3-CDR3-1/VL2-CDR3-3 | 3.31E-09 | ND | ND |

FIG._6A

Heavy / Light Chain Pairs

| Antibody | Heavy Chain / Light Chain | Approximate Affinity in BIAcore to Human MN Proteoglycan Peptide Labeled BSA | Inhibition of ELISA Signal with Proteoglycan Peptide B (1mg/ml) | Inhibition in MN Cell Binding Assay (100 ug/ml Fab) |
|---|---|---|---|---|
| 25 | VH3-CDR1-3/VH3-CDR3-1/VL2-CDR3-3 | 4.89E-09 | ND | ND |
| 26 | VH3-CDR1-4/VH3-CDR3-1/VL2-CDR3-3 | 3.57E-09 | ND | ND |
| 27 | VH3-CDR3-1/VL2-CDR1-1/VL2-CDR3-3 | 9.47E-09 | ND | ND |
| 28 | VH3-CDR3-1/VL2-CDR1-2/VL2-CDR3-3 | 3.95E-09 | ND | ND |
| 29 | VH3-CDR3-11/VL2-CDR3-4 | 8.19E-09 | ND | ND |
| 30 | VH3-CDR3-1/VL2-CDR3-4 | 3.91E-09 | ND | ND |
| 31 | VH3-CDR3-12/VL2-CDR3-4 | 1.23E-09 | ND | ND |
| 32 | VH3-CDR3-13/VL2-CDR3-4 | 1.34E-09 | ND | ND |
| 33 | VH3-CDR3-14/VL2-CDR3-4 | 1.23E-09 | ND | ND |
| 34 | VH3-CDR3-15/VL2-CDR3-4 | 1.61E-09 | ND | ND |
| 35 | VH3-CDR3-16/VL2-CDR3-4 | 1.31E-09 | ND | ND |
| 36 | VH3-CDR3-17/VL2-CDR3-4 | 2.87E-09 | ND | ND |
| 37 | VH3-CDR3-18/VL2-CDR3-4 | 2.82E-09 | ND | ND |
| 38 | VH3-CDR3-19/VL2-CDR3-4 | 1.43E-09 | ND | ND |
| 39 | VH3-CDR3-20/VL2-CDR3-4 | 1.55E-09 | ND | ND |
| 40 | VH3-CDR3-1/VL2-CDR3-3/VH3-CDR1-1 | 1.82E-08 | ND | ND |
| 41 | VH3-CDR3-1/VL2-CDR3-3/VH3-CDR1-2 | 5.70E-09 | ND | ND |
| 42 | VH3-CDR3-1/VL2-CDR3-3/VH3-CDR1-3 | 6.00E-10 | ND | ND |
| 43 | VH3-CDR3-1/VL2-CDR3-3/VH3-CDR1-4 | N.D. | ND | ND |
| 44 | VH3-CDR3-1/VL2-CDR3-3/VH3-CDR1-5 | 2.00E-09 | ND | ND |
| 45 | VH3-CDR3-1/VL2-CDR3-3/VH3-CDR1-6 | 6.00E-10 | ND | ND |
| 46 | VH3-CDR3-1/VL2-CDR3-3/VH3-CDR1-7 | 8.00E-10 | ND | ND |
| 47 | VH3-CDR3-1/VL2-CDR3-3/VH3-CDR1-8 | 4.10E-09 | ND | ND |
| 48 | VH3-CDR3-1/VL2-CDR3-3/VH3-CDR1-9 | 1.20E-09 | ND | ND |
| 49 | VH3-CDR3-1/VL2-CDR3-3/VH3-CDR1-10 | 1.00E-09 | ND | ND |

FIG._6B

HUMAN ANTIBODIES THAT HAVE MN BINDING AND CELL ADHESION-NEUTRALIZING ACTIVITY

This application claims priority to and incorporates by reference provisional application Ser. No. 60/343,657 filed Oct. 18, 2001, and provisional application Ser. No. 60/377,716 filed May 3, 2002.

This application incorporates by reference the sequence listing contained on a compact disc, which is part of this application. The sequence listing is a 1.44 MB ASCII file named "Human Antibodies That Have Mn Binding And Cell Adhesion-Neutralizing Activity", created on Oct. 3, 2002

FIELD OF THE INVENTION

This invention relates to MN binding human antibodies

BACKGROUND OF THE INVENTION

MN is a cell surface protein that is detected in a number of clinical carcinoma samples but is absent in the normal tissue of the corresponding organs. The MN cDNA has been cloned (Pastorek, J. et al, *Oncogene* (1994), 9, 2877-2888) and the predicted protein consists of a signal peptide, a proteoglycan-related sequence, a carbonic anhydrase domain, a transmembrane segment, and a short intracellular tail. MN is normally expressed in stomach and bile duct mucosa (Liao, S. Y., et al, *Am J Pathol* (1994), 145, 598-609) and in highly proliferative normal cells located in the small intestine (Saarnio, J. et al, *J Histochem Cytochem* (1998) 46, 497-504). However, MN is ectopically expressed in 100% renal cell carcinomas (Liao, S. Y., *Cancer Res* (1997) 57, 2827-2831), 100% of carcinomas of the esophagus (Turner, J. R. *Hum Pathol,* (1997) 28, 740-744), greater than 90% of cervical carcinomas (Liao, S. Y., et al, *Am J Pathol* (1994), 145, 598-609), 76% of malignant colon carcinomas, (Saarnio, J. et al, *Am J Pathol* (1998) 153, 279-285), 80% of non-small cell lung carcinomas (Vermylen, P. et al, *Eur Respir J* (1999), 14, 806-811), and in 48% of breast cancers (Chia, S. K. et al, *J. Clin. Oncol* (2001) 19, 3660-3668).

Antibodies against MN have been described. Mouse monoclonal antibody G250 is effective in the reduction of renal cell carcinoma tumor size in a mouse model (van Dijk, J. et al, *Int. J. Cancer* (1994) 56, 262-268). This antibody was subsequently made into a chimeric antibody containing human Fc regions and the mouse variable regions. The chimeric G250 antibody is only 66% human, leading to a greater chance of immunogenicity in humans compared to a comparable fully human antibody. Therefore, treatment with the 33% mouse antibody may lead to a human anti-mouse immunogenic response, rendering the anti-cancer treatment ineffective. These problems with chimeric antibodies clearly raise the need for fully human antibodies against MN.

BRIEF SUMMARY OF THE INVENTION

The invention is composed of monoclonal human MN antibodies or MN antibody fragments that target the GEEDLP (SEQ ID NO 118) repeat within the proteoglycan domain. The proteoglycan domain of the MN cell surface protein contains four of these identical GEEDLP (SEQ ID NO 118) repeats. Binding to the desired epitope is verified by competition ELISA, where ELISA signal can be attenuated by co-incubation with a peptide containing this repeat (PGEEDLPGEEDLP) (SEQ ID NO 119). This inhibition of binding can also be verified using Biacore assays, where binding of desired antibodies to immobilized MN or proteoglycan peptides can be inhibited by the peptide repeat. In addition to binding to the peptide repeat, human anti-MN antibodies can inhibit the cell adhesion of CGL-1 cells to MN coated plastic plates. Human anti-MN antibodies have been used to diagnose and quantify MN expression in cancer cells and tumors using FACS and immunohistochemical methods. An example is also provided where a human anti-MN IgG1 mediates tumor cell lysis though antibody-dependent cell-mediated cytotoxicity. Therefore, these antibodies will be useful for the treatment of cancers in which MN is upregulated or can be useful for the diagnosis of cancers in which MN is upregulated.

BRIEF DESCRIPTION OF THE DRAWINGS

FIG. 1 PC3mm2 human prostate cancer cells express MN as assayed by FACS.

FIG. 2 Sequence identifications for SEQ ID #1 through SEQ ID #83

FIG. 3 Fab display vector pMORPH18 Fab 1

FIG. 4 Vector map of pMORPHx9_Fab1_FS

FIG. 5 Images of Blocking of Cell Adhesion with Anti-MN Antibody MN-3

FIG. 6 Antibody binding pairs for MN antibodies 1 through 39. BIAcore binding affinity is displayed.

DETAILED DESCRIPTION OF THE INVENTION

The invention provides human antibodies that bind to MN. These antibodies are useful for a variety of therapeutic and diagnostic purposes. These purposes include:

Characteristics of Human MN Antibodies

"Antibody" as used herein includes intact immunoglobulin molecules (e.g., IgG1 IgG2a, IgG2b, IgG3, IgM, IgD, IgE, IgA), as well as fragments thereof, such as Fab, F(ab')$_2$, scFv, and Fv, which are capable of specific binding to an epitope of a human MN protein. Antibodies that specifically bind to MN provide a detection signal at least 5-,10-, or 20-fold higher than a detection signal provided with other proteins when used in an immunochemical assay. Preferably, antibodies that specifically bind to human MN do not detect other proteins in immunochemical assays and can immunoprecipitate the MN from solution.

References to VL2 and/or VL3 in this specification are intended to denote the lambda ($\lambda$) class of light chain.

The $K_d$ of human antibody binding to MN can be assayed using any method known in the art, including technologies such as real-time Bimolecular Interaction Analysis (BIA) (Sjolander & Urbaniczky, *Anal. Chem.* 63, 2338-2345, 1991, and Szabo et al., *Curr. Opin. Struct. Biol.* 5, 699-705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In a BIAcore™ assay, human antibodies of the present invention specifically bind to human MN with a $K_d$ in the range from about 0.6 nM ($6 \times 10^{-10}$ nM) to about 1800 nM ($1.8 \times 10^{-6}$ nM) see FIG. 6. More preferred human antibodies of the present invention specifically bind to human MN with a $K_d$ of approximately 0.6 nM to about 90 nM, with the most preferred antibodies of this invention binding human MN protein with a $K_d$ of approximately 4 nM.

Preferably, antibodies of this invention as envisioned will bind to the GEEDLP (SEQ ID NO 118) repeat within the proteoglycan domain, which contains four of these identical repeats. Binding to the desired epitope can be verified using any method known in the art, including techniques like competition ELISA (Zavada et al, Br. J. of Cancer 82, 1808-1813, 2000), where ELISA signal can be attenuated by co-incubation with a peptide containing this repeat (PGEEDLP-GEEDLP), (SEQ ID NO 119) but not inhibited by a similar peptide (PSEEDSPREEDP) (SEQ ID NO 120), which is also within the proteoglycan domain. This pattern of binding inhibition also can be verified using BlAcore™ technologies, where binding of desired antibodies to immobilized MN or proteoglycan peptides can be inhibited by incubation with the peptide repeat. Preferably antibodies of this invention also can inhibit the cell adhesion of MN expressing cells to MN coated plastic plates ELISA (Zavada et al, Br. J. of Cancer 82, 1808-1813, 2000).

This invention uses Morphosys phage-antibody technology to generate fully human antibodies against the MN protein. The Morphosys library is based upon human backbones, greatly reducing the probability of immunogenicity.

A number of human antibodies having the MN binding and cell adhesion neutralizing characteristics described above have been identified by screening the MorphoSys HuCAL Fab library. The CDR cassettes assembled for the HuCAL library were designed to achieve a length distribution ranging from 5 to 28 amino acid residues, covering the stretch from position 95 to 102. Knappik et al., *J. Mol. Biol.* 296, 57-86, 2000. Knappik et al., *J. Mol. Biol.* 296, 57-86, 2000. In some embodiments of the invention, the VH3-CDR3 region of a human antibody has an amino acid sequence shown in FIG. 2 in SEQ ID NOS: 61-80. In other embodiments of the invention, the VLλ1-CDR3, VLλ2-CDR3, and VLλ2-CDR1 regions of a human MN antibody has amino acid sequences as shown shown in FIG. 2 in SEQ ID NOS: 81-89 with optimized VH3-CDR1 sequences as shown in SEQ ID NOS: 48-60, both are shown in FIG. 2. Human antibodies that have MN binding and cell adhesion-neutralizing activity are as shown in Tables 1 and 2; the variable regions within these antibodies (the CDR3 loops) are shown in Tables 1 & 2.

Obtaining Human Antibodies

Human antibodies with the MN binding and cell adhesion-neutralizing activity described above can be identified from the MorphoSys HuCAL library as follows. Human MN is coated on a microtiter plate and incubated with the MorphoSys HuCAL-Fab phage library (see: Example 1). Those phage-linked Fabs not binding to MN can be washed away from the plate, leaving only phage that tightly bind to MN. The bound phage can be eluted by a change in pH and amplified by infection of *E. coli* hosts. This panning process can be repeated once or twice to enrich for a population of phage-linked antibodies that tightly bind to MN. The Fabs from the enriched pool are then expressed, purified, and screened in an ELISA assay. The identified hits are then tested for binding using a BIAcore™ assay, and these hits can be further screened in the cell adhesion assay as described above.

The initial panning of the HuCAL-Fab library also can be performed with MN as the antigen in round one, followed in round 2 by MN peptides fused to carrier proteins, such as BSA or transferrin, and in round 3 by MN antigen again. Human MN peptides that can be used for panning include human MN SEQ I.D. 45-47. These peptide sequences are derived from the MN proteoglycan sequence, which are thought to be involved in cell adhesion.

Alternatively, panning could be performed using MN expressing cells as antigen. For example, cells transfected with MN antigen can be labeled with biotin. These transfected cells are then mixed with unlabled, non-MN transfected cells at a labeled: unlabeled ratio of 1:10. The phage library is added to the cells, and the biotinylated, MN-bearing cells are captured with streptavidin-bound magnetic beads that are bound to a magnet. Non-specific phage are washed away, and the MN-bearing cells are specifically eluted by removing the magnetic field. These specifically bound phage can be amplifed for further rounds of cell panning or can be alternated with peptide and/or protein panning.

Details of the screening process are described in the specific examples, below. Other selection methods for highly active specific antibodies or antibody fragments can be envisioned by those skilled in the art and used to identify human MN antibodies.

Human antibodies with the characteristics described above also can be purified from any cell that expresses the antibodies, including host cells that have been transfected with antibody-encoding expression constructs. The host cells are cultured under conditions whereby the human antibodies are expressed. A purified human antibody is separated from other compounds that normally associate with the antibody in the cell, such as certain proteins, carbohydrates, or lipids, using methods well known in the art. Such methods include, but are not limited to, size exclusion chromatography, ammonium sulfate fractionation, ion exchange chromatography, affinity chromatography, and preparative gel electrophoresis. A preparation of purified human antibodies is at least 80% pure; preferably, the preparations are 90%, 95%, or 99% pure. Purity of the preparations can be assessed by any means known in the art, such as SDS-polyacrylamide gel electrophoresis. A preparation of purified human antibodies of the invention can contain more than one type of human antibody with the MN binding and neutralizing characteristics described above.

Alternatively, human antibodies can be produced using chemical methods to synthesize its amino acid sequence, such as by direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of human antibodies can be separately synthesized and combined using chemical methods to produce a full-length molecule.

The newly synthesized molecules can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic polypeptide can be confirmed by amino acid analysis or sequencing (e.g., using Edman degradation).

Assessment of Therapeutic Utility of Human Antibodies To assess the ability of a particular antibody to be therapeutically useful to treat cancer, as an example, the antibody can be tested in vivo in a mouse xenograft tumor model. If desired, human Fab MN antibodies can be converted into $IgG_1$ antibodies before therapeutic assessment. This conversion is described in Example 5, and an example of a therapeutic model is detailed in Example 9. Utility also can be tested using an antibody dependent cell-mediated cytotoxicity assay as described in Example 13.

Polynucleotides Encoding Human MN Antibodies

The invention also provides polynucleotides encoding human MN antibodies. These polynucleotides can be used, for example, to produce quantities of the antibodies for therapeutic or diagnostic use.

Polynucleotides that can be used to encode the VH-CDR3 regions shown in SEQ ID NOS: 14-33. Polynucleotides that can be used to encode the VL-CDR3 regions shown are shown in SEQ ID NOS: 34-44. Polynucleotides that encode heavy chains and light chains of human antibodies of the invention that have been isolated from the MorphoSys HuCAL library are shown in FIG. 2. Additional optimized VH3-CDR1 sequences are shown in SEQ ID NOS: 1-13.

Polynucleotides of the invention present in a host cell can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated polynucleotides encoding antibodies of the invention. For example, restriction enzymes and probes can be used to isolate polynucleotides which encode the antibodies. Isolated polynucleotides are in preparations that are free or at least 70, 80, or 90% free of other molecules.

Human antibody-encoding cDNA molecules of the invention can be made with standard molecular biology techniques, using mRNA as a template. Thereafter, cDNA molecules can be replicated using molecular biology techniques known in the art and disclosed in manuals such as Sambrook et al. (1989). An amplification technique, such as PCR, can be used to obtain additional copies of the polynucleotides.

Alternatively, synthetic chemistry techniques can be used to synthesize polynucleotides encoding antibodies of the invention. The degeneracy of the genetic code allows alternate nucleotide sequences to be synthesized that will encode an antibody having, for example one of the VH-CDR3, VH-CDR1 or VL-CDR3, light chain or heavy chain amino acid sequences shown in SEQ ID NOS: 48-89 respectively.

Expression of Polynucleotides

To express a polynucleotide encoding a human antibody of the invention, the polynucleotide can be inserted into an expression vector that contains the necessary elements for the transcription and translation of the inserted coding sequence. Methods that are well known to those skilled in the art can be used to construct expression vectors containing sequences encoding human antibodies and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1995. See also Examples 1-3, below.

A variety of expression vector/host systems can be utilized to contain and express sequences encoding a human antibody of the invention. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a human antibody, vectors based on SV40 or EBV can be used with an appropriate selectable marker.

Pharmaceutical Compositions

Any of the human MN antibodies described above can be provided in a pharmaceutical composition comprising a pharmaceutically acceptable carrier. The pharmaceutically acceptable carrier preferably is non-pyrogenic. The compositions can be administered alone or in combination with at least one other agent, such as stabilizing compound, which can be administered in any sterile, biocompatible pharmaceutical carrier, including, but not limited to, saline, buffered saline, dextrose, and water. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. See U.S. Pat. No. 5,851,525. If desired, more than one type of human antibody, for example with different $K_d$ for MN binding, can be included in a pharmaceutical composition.

The compositions can be administered to a patient alone, or in combination with other agents, drugs or hormones. In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

After pharmaceutical compositions have been prepared, they can be placed in an appropriate container and labeled for treatment of an indicated condition. Such labeling would include amount, frequency, and method of administration.

Diagnostic Methods

The invention also provides diagnostic methods, with which human MN can be detected in a test preparation, including without limitation a sample of serum, lung, liver, heart, breast, kidney, colon, a cell culture system, or a cell-free system (e.g., a tissue homogenate). Such diagnostic methods can be used, for example, to diagnose disorders in which MN is elevated. Such disorders include, but are not limited to carcinomas of the kidney, esophagus, breast, cervix, colon, and lung. When used for diagnosis, detection of an amount of the antibody-MN complex in a test sample from a patient which is greater than an amount of the complex in a normal sample identifies the patient as likely to have the disorder. An immunohistochemical method for the detection of MN in cancer tissues is described in Example 12.

The test preparation is contacted with a human antibody of the invention, and the test preparation is then assayed for the presence of an antibody-MN complex. If desired, the human antibody can comprise a detectable label, such as a fluorescent, radioisotopic, chemiluminescent, or enzymatic label, such as horseradish peroxidase, alkaline phosphatase, or luciferase. A fluorescence-based assay for the detection of MN expressing tumor cells is shown in Example 11.

Optionally, the antibody can be bound to a solid support, which can accommodate automation of the assay. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the antibody to the solid support, including use of covalent and non-covalent linkages, passive absorption, or pairs of binding moieties attached to the antibody and the solid support. Binding of MN and the antibody can be accomplished in any vessel suitable for containing the reactants. Examples of such vessels include microtiter plates, test tubes, and microcentrifuge tubes.

Therapeutic Methods

The invention also provides methods of ameliorating symptoms of a disorder in which MN is elevated. These disorders include, without limitation, carcinomas of the kidney, esophagus, breast, cervix, colon, and lung. See, e.g., (Liao, S. Y., *Cancer Res* (1997) 57, 2827-2831), (Turner, J. R. *Hum Pathol*, (1997) 28, 740-744), (Liao, S. Y., et al, *Am J Pathol* (1994), 145, 598-609), (Saarnio, J. et al, *Am J Pathol* (1998) 153, 279-285), and (Vermylen, P. et al, *Eur Respir J* (1999), 14, 806-811).

In one embodiment of the invention, a therapeutically effective dose of a human antibody of the invention is administered to a patient having a disorder in which MN is elevated, such as those cancers described above.

Determination of a Therapeutically Effective Dose

The determination of a therapeutically effective dose is well within the capability of those skilled in the art. A therapeutically effective dose refers to the amount of human antibody that is used to effectively treat a cancer compared with the efficacy that is evident in the absence of the therapeutically effective dose.

The therapeutically effective dose can be estimated initially in animal models, usually rats, mice, rabbits, dogs, or pigs. The animal model also can be used to determine the appropriate concentration range and route of administration. Such information can then be used to determine useful doses and routes for administration in humans. A subcutaneous mouse xenograft model is described in Example 9.

Therapeutic efficacy and toxicity, e.g., $ED_{50}$ (the dose therapeutically effective in 50% of the population) and $LD_{50}$ (the dose lethal to 50% of the population) of a human antibody, can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the patient who requires treatment. Dosage and administration are adjusted to provide sufficient levels of the human antibody or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Polynucleotides encoding human antibodies of the invention can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding the antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

The mode of administration of human antibody-containing pharmaceutical compositions of the invention can be any suitable route which delivers the antibody to the host. Pharmaceutical compositions of the invention are particularly useful for parenteral administration, i.e., subcutaneous, intramuscular, intravenous, or intranasal administration.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Construction of a Human Combinatorial Antibody Library (HuCAL-Fab 1)

Cloning of HuCAL-Fab 1. HuCAL-Fab 1 is a fully synthetic, modular human antibody library in the Fab antibody fragment format. HuCAL-Fab 1 was assembled starting from an antibody library in the single-chain format (HuCAL-scFv; Knappik et al., *J. Mol. Biol.* 296 (2000) 55). HuCAL-Fab 1 was cloned into a phagemid expression vector pMORPH18 Fab1 (FIG. 3). This vector comprises the Fd fragment with a phoA signal sequence fused at the C-terminus to a truncated gene III protein of filamentous phage, and further comprises the light chain VL-CL with an ompA signal sequence. Both chains are under the control of the lac operon. The constant domains Cλ, Ck, and CH are synthetic genes fully compatible with the modular system of HuCAL (Knappik et al., 2000).

First, the Vλ and Vκ libraries were isolated from HuCAL-scFv by restriction digest using EcoRWDraIII and EcoRWB-siWI, respectively. These Vλ and Vκ libraries were cloned into pMORPH18 Fab1 cut with EcoRWDraIII and EcoRWB-siWI, respectively. After ligation and transformation in E. coli TG-1, library sizes of $4.14 \times 10^8$ and $1.6 \times 10^8$, respectively, were obtained, in both cases exceeding the VL diversity of HuCAL-scFv.

Similarly, the VH library was isolated from HuCAL-scFv by restriction digest using StyI/MunI. This VH library was cloned into the pMORPH18-Vλ and Vκ libraries cut with StyI/MunI. After ligation and transformation in E. coli TG-1, a total library size of $2.09 \times 10^{10}$ was obtained, with 67% correct clones (as identified by sequencing of 207 clones).

Phagemid rescue, phage amplification and purification. HuCAL-Fab was amplified in 2×TY medium containing 34 µg/ml chloramphenicol and 1% glucose (2×TY-CG). After helper phage infection (VCSM13) at 37° C. at an OD600 of about 0.5, centrifugation and resuspension in 2×TY/34 µg/ml chloramphenicol/50 µg/ml kanamycin, cells were grown overnight at 30° C. Phage were PEG-precipitated from the supernatant (Ausubel et al., 1998), resuspended in PBS/20% glycerol, and stored at −80° C. Phage amplification between two panning rounds was conducted as follows: mid-log phase TG1-cells were infected with eluted phage and plated onto LB-agar supplemented with 1% of glucose and 34 µg/ml of chloramphenicol. After overnight incubation at 30° C., colonies were scraped off and adjusted to an OD600 of 0.5. Helper phage were added as described above.

EXAMPLE 2

Solid Phase Panning

Wells of MaxiSorp™ microtiter plates (Nunc) were coated with human MN protein in PBS (2 µg/well). After blocking with 5% non-fat dried milk in PBS, 1-5×1012 HuCAL-Fab phage purified as above were added for 1 h at 20° C. After several washing steps, bound phage were eluted by pH-elution with 100 mM triethylamine and subsequent neutralization with 1M TRIS-Cl pH 7.0. Three rounds of panning were performed with phage amplification conducted between each round as described above.

EXAMPLE 3

Subcloning of Selected Fab Fragments for Expression

The Fab-encoding inserts of the selected HuCAL Fab fragments were subcloned into the expression vector pMORPHx7_FS to facilitate rapid expression of soluble Fab. The DNA preparation of the selected HuCAL Fab was digested with XbaI/EcoRI, thus cutting out the Fab encoding insert (ompA-VL and phoA-Fd). Subcloning of the purified inserts into the XbaI/EcoRI cut vector pMORPHx7, previously carrying a scFv insert, leads to a Fab expression vector designated pMORPHx9_Fab1_FS (FIG. 4). Fabs expressed in this vector carry two C-terminal tags (FLAG and Strep) for detection and purification.

EXAMPLE 4

Identification of MN-Binding Fab Fragments by ELISA

The wells of a Maxisorp ELISA plates were coated with 100 µl/well solutions of human MN at a concentration of 5 µg/ml diluted in coating buffer. Expression of individual Fab was induced with 0.5 mM IPTG for 12 h at 30° C. Soluble Fab was extracted from the periplasm by osmotic shock (Ausubel et al., 1998) and used in an ELISA. The Fab fragment was detected with an anti-Fab antibody (Dianova). Values at 370 nm were read out after addition of horseradish peroxidase-conjugated anti-mouse IgG antibody and POD soluble substrate (Roche Diagnostics).

EXAMPLE 5

Construction of HuCAL Immunoglobulin Expression Vectors

Heavy chain cloning. The multiple cloning site of pcDNA3.1+ (Invitrogen) was removed (NheI/ApaI), and a stuffer compatible with the restriction sites used for HuCAL design was inserted for the ligation of the leader sequences (NheI/EcoRI), VH-domains (EcoRI/BlpI), and the immunoglobulin constant regions (BlpI/ApaI). The leader sequence (EMBL M83133) was equipped with a Kozak sequence (Kozak, 1987). The constant regions of human IgG1 (PIR J00228), IgG4 (EMBL K01316), and serum IgA1 (EMBL J00220) were dissected into overlapping oligonucleotides with lengths of about 70 bases. Silent mutations were introduced to remove restriction sites non-compatible with the HuCAL design. The oligonucleotides were spliced by overlap extension-PCR.

Light chain cloning. The multiple cloning site of pcDNA3.1/Zeo+ (Invitrogen) was replaced by two different stuffers. The κ-stuffer provided restriction sites for insertion of a κ-leader (NheI/EcoRV), HuCAL-scFv Vk-domains (EcoRV/BsiWI,) and the κ-chain constant region (BsiWI/ApaI). The corresponding restriction sites in the κ-stuffer were NheI/EcoRV (I-leader), EcoRV/HpaI (Vl-domains), and HpaI/ApaI (λ-chain constant region). The κ-leader (EMBL Z00022) as well as the λ-leader (EMBL L27692) were both equipped with Kozak sequences. The constant regions of the human κ-(EMBL J00241) and λ-chain (EMBL M18645) were assembled by overlap extension-PCR as described above.

Generation of IgG-expressing CHO-cells. CHO-K1 cells were co-transfected with an equimolar mixture of IgG heavy and light chain expression vectors. Double-resistant transfectants were selected with 600 µg/ml G418 and 300 µg/ml Zeocin (Invitrogen) followed by limiting dilution. The supernatant of single clones was assessed for IgG expression by capture-ELISA (see below). Positive clones were expanded in RPMI-1640 medium supplemented with 10% ultra-low IgG-FCS (Life Technologies). After adjusting the pH of the supernatant to 8.0 and sterile filtration, the solution was subjected to standard protein A column chromatography (Poros 20 A, PE Biosystems).

EXAMPLE 6

Design of the CDR3 Libraries

Vλ positions 1 and 2. The original HuCAL master genes were constructed with their authentic N-termini: VLλ1: QS (CAGAGO) (SEQ ID NO 121), VLλ2: QS (CAGAGC) (SEQ ID NO 121), and VLλ3: SY (AGCTAT) (SEQ ID NO 122). Sequences containing these amino acids are shown in WO 97/08320. During HuCAL library construction, the first two amino acids were changed to Dl to facilitate library cloning (EcoRI site). All HuCAL libraries contain VLλ genes with the EcoRV site GATATC (SEQ ID NO 122) (Dl) at the 5'-end. All HuCAL kappa genes (master genes and all genes in the library) contain Dl at the 5'-end.

VH position 1. The original HuCAL master genes were constructed with their authentic N-termini: VH1A, VH1 B, VH2, VH4, and VH6 with Q (=CAG) as the first amino acid and VH3 and VH5 with E (=GAA) as the first amino acid. Sequences containing these amino acids are shown in WO 97/08320. In the HuCAL Fab 1 library, all VH chains contain Q (=CAG) at the first position.

Vκ1/Vκ3 position 85. Because of the cassette mutagenesis procedure used to introduce the CDR3 library (Knappik et al., *J. Mol. Biol.* 296, 57-86, 2000), position 85 of Vκ1 and Vκ3 can be either T or V. Thus, during HuCAL scFv 1 library construction, position 85 of Vκ1 and Vκ3 was varied as follows: Vk1 original, 85T (codon ACC);

Vκ1 library, 85T or 85V (TRIM codons ACT or GTT); Vκ3 original, 85V (codon GTG); Vκ3 library, 85T or 85V (TRIM codons ACT or GTT); the same applies to HuCAL Fab1.

CDR3 design. All CDR3 residues which were kept constant are indicated in Tables 1 & 2 (SEQ ID NOS 90-117).

CDR3 length. The designed CDR3 length distribution is as follows. Residues which were varied are shown in the Sequence Listing as shown in FIG. 2. V kappa CDR3, 8 amino acid residues (position 89 to 96) (occasionally 7 residues), with Q90 fixed; V lambda CDR3, 8 to 10 amino acid residues (position 89 to 96) (occasionally 7-10 residues), with Q89, S90, and D92 fixed; and VH CDR3, 5 to 28 amino acid residues (position 95 to 102) (occasionally 4-28), with D101 fixed.

EXAMPLE 7

Competition ELISA for Epitope Mapping

Nunc Maxisorb microtiter plates were coated overnight at 4° C. with 100 µL of MN or MN-peptide-coupled BSA in PBS at a concentration of 5 µg/mL. Each well is blocked with 5% non-fat milk in PBS for 2 hours at RT on a microtiter plate shaker. The plate is washed with PBS with 0.05% Tween-20. 200 µL per well of antibody or antibody+proteoglycan peptide A, B, or C (SEQ ID 20-22) is added to the well. Antibody and proteoglycan peptide concentrations were optimized to yield greatest ease in determining the 50% end point. These antibody/peptide mixtures were incubated for 1.5 hours at RT on a microtiter plate shaker. The ELISA plates are washed 5× quickly with TBS containing 0.05% Tween-20. Bound antibody was tested using peroxidase conjugated goat anti-Fab IgG (Sigma). After further washing with TBS-Tween, 100 µL of BM Blue POD Substrate (Roche) is added. After 30 minutes of incubation, the absorbance is read at 370 nm.

EXAMPLE 8

Cell Adhesion Assay

1 µg/mL of purified MN in 50 mM bicarbonate buffer pH 9.2 was adsorbed in 30 µL drops on the bottom of bacteriological 5 cm Petri dishes for 1.5 hours. The drops were removed and rinsed 3 times with PBS. Subsequently the drops were blocked with 50% fetal calf serum in DMEM. The drops were further treated with 30 mL of 20-100 µg/mL anti-MN IgGs or with PBS and irrelevant antibodies as a control. After washing the drops with PBS, the spots were incubated with 30 µL of CGL-1 cell suspension (105 cells/mL) and incubated overnight. The ability of anti-MN antibodies to block adhesion of CGL-1 cells to MN coated plates was assessed after washing the drops with PBS. An example of this experiment in shown in FIG. 5 where 20 µg/ml of Anti-MN antibody MN-3 (FIG. 5A) inhibits cell adhesion compared to control gamma globulin (FIG. 5B) and to no antibody treatment (FIG. 5C).

EXAMPLE 9

Subcutaneous Xenograft Cancer Model

Antitumor effects of anti-MN antibodies were evaluated using subcutaneous xenograft models in immunodeficient mice. HT-29 cells were maintained as adherent cultures in DMEM supplemented with 10% FBS. SCID mice of 6-7 weeks age were inoculated subcutaneously in the right flank with $1 \times 10^7$ cells in 0.1 mL of medium. Monoclonal antibodies were administered i.p. daily at a dose of 500 µg. Control mice were treated with PBS or an irrelevant monoclonal antibody. Tumors were measured twice a week with a sliding caliper. Anti-tumor efficacy was evaluated by comparing the tumor size of anti-MN antibody treatment versus control treatment.

EXAMPLE 10

Subcutaneous Xenograft Cancer Model with Immunoconjugate

Anti-MN antibodies were conjugated to cytotoxic small molecules using protocols that are known in the art (e.g. C. Liu et al., *Proc. Natl. Acad. Sci.* (1996), 93, 8618-8623.) HT-29 cells were maintained as adherent cultures in DMEM supplemented with 10% FBS. Female CB-17 SCID mice, 6-7 weeks of age were inoculated subcutaneously at the right flank with 1×10e7 tumor cells in 0.1 mL of medium. After tumor sizes reach from 65 mm³, animals were injected daily with 0.5 mg of antibody conjugate for five consecutive days. Control mice were treated with PBS, an irrelevant monoclonal antibody, or free unconjugated drug. Tumors were measured twice a week with a sliding caliper. Anti-tumor efficacy was evaluated by comparing the tumor size of anti-MN antibody treatment versus control treatment.

EXAMPLE 11

Fluorescence-Activated Cell Sorting Assay (FACS Assay)

Cells can be assayed for MN expression as a diagnostic tool. For adherent cell lines, detach cells from their flask by first removing their culture medium, rinsing them once with ice cold PBS, and treating them with 1 mM EDTA in PBS for 5 to 10 min depending on the cell line (encourage by periodically tapping the flask). Spin the cells down (1500 rpm, 5 min) and wash the cells once with ice cold Staining Buffer (10% FBS, 0.1% sodium azide, PBS). Resuspend the cells in ice-cold Staining Buffer at 1 million cells in 200 ul. Add the primary antibody at 3.2 E-11 to 3.2 E-8 M and incubate on ice for 1 h. Wash the unbound antibody with the ice-cold Staining Buffer. Resuspend the cell pellet in 200 ul of ice cold Staining Buffer and add 20 ul per 200 ul of cells of FITC-conjugated anti-human secondary antibody (Pharmingen). Incubate on ice for 1 h. Wash the unbound antibody and resuspend the cells in 200 ul of 2.5 ug/ml Propidium Iodide (PI) (Sigma) in the Staining Buffer (to gate for dead cells). Proceed with the FACS analysis gating out the cells that take up PI. PC3mm2 human prostate cancer cells express MN as assayed by FACS as shown in FIG. 7. The red line represents staining with human anti-MN antibody, while the black line represents a control, isotype-matched human antibody.

EXAMPLE 12

Immunohistochemical Analysis of Tumor Samples

Tumor sections can be tested for MN expression. Since MN is highly expressed in cancer and low expression levels are present in normal tissue, analyzing MN expression is of utility for the diagnosis and detection of cancer in patient samples. For analysis of tissue sections, standard immunohistochemical techniques can be used. Tissue sections containing a PC-3 prostate carcinoma were implanted in SCID mice. 20 micrograms/mL of anti-MN antibody was incubated with the dewaxed paraffin section and the slide was developed using a peroxidase conjugated secondary antibody, and developed using DAB chromogen. A strong membrane-associated signal was readily observed and is characteristic of high MN expression in the prostate cancer cells.

EXAMPLE 13

Antibody-Dependent Cell Mediated Cytotoxicity Assays (ADCC Assays)

Anti-tumor activity of anti-MN IgGgs can be mediated by ADCC activity. MN-expressing PC-3 mm2 cells and non-MN expressing HCT-116 cells are incubated with 250 ng/mL, 1000 ng/mL or 2000 ng/mL human anti-MN IgG1 or control human IgG1 anti-digoxin antibody. Human PBMCs are added to these cells at effector: target ratios of 50:1, 25:1, and 5:1 ratios. A chromium-51 release assay is performed to determine the level of target cell lysis. A small amount of lysis is observed upon incubation of control antibody or no antibody in the presence of HCT-116 or PC-3 mm2 cells. This spontaneous level of lysis is 10-15%, 5-10%, or 2-3% for 50:1, 25:1, and 5:1 target effector ratios respectively. Similarly, lysis of non-MN expressing HCT-116 cells was in the 0-10% range when incubated with the anti-MN antibodies. However, lysis of PC-3 mm2 cells when incubated with the human anti-MN IgGs was significantly higher than the controls. Lysis of 40, 50, and 60% was observed when using 250 ng/mL, 1000 ng/mL and 2000 ng/mL at 50:1 target:effector ratios. Similarly, 30, 33, and 38% lysis was observed at 25:1 ratios, and finally, 8, 10, and 15% lysis was observed at 5:1 target:effector ratios. These experiments show that human anti-MN antibodies mediate anti-tumor ADCC activity and may be used for the therapeutic treatment of cancer.

We claim:

1. A purified preparation of a human antibody comprising:
   a) a variable heavy chain comprising an amino acid sequence of SEQ ID NO: 100, wherein
      the variable heavy chain CDR3 region of SEQ ID NO: 100 is replaced by an amino acid sequence selected from the group consisting of SEQ ID NOS: 61, 62, 63, 64, 65, 66, 67, 68, 69, 70, 71, 72, 73, 74, 75, 76, 77, 78, 79, and 80, and
      the variable heavy chain CDR1 region of SEQ ID NO: 100 is optionally replaced by an amino acid sequence selected from the group consisting of SEQ ID NOS: 48, 49, 50, 51, 52, 53, 54, 55, 56, 57, 58, 59, and 60; and
   b) a variable light chain comprising an amino acid sequence of SEQ ID NO: 94 or 95, wherein
      the variable light chain CDR3 region of SEO ID NO: 94 or 95 is replaced by an amino acid sequence selected from the group consisting of SEQ ID NOS: 81, 84, 85, 86, 87, 88, and 89, and
      the variable light chain CDR1 region of SEQ ID NO: 94 or 95 is optionally replaced by an amino acid sequence of SEQ ID NO: 82 or 83, wherein the antibody binds to a GEEDLP (SEQ ID NO: 118) repeat region within a MN protein's proteoglycan domain.

2. The purified preparation of claim 1 wherein the variable heavy chain CDR3 region is the amino acid of SEQ ID NO: 64.

3. The purified preparation of claim 1 wherein the variable light chain CDR3 region is the amino acid sequence of SEQ ID NO: 81.

4. The purified preparation of claim 1 wherein the variable light chain CDR3 region is the amino acid sequence selected from the group consisting of SEQ ID NOS: 84, 85, 86, 87, 88, and 89.

5. The purified preparation of claim 1 wherein the variable heavy chain CDR3 region and the variable light chain CDR3 region, respectively, are the amino acid sequence pairs selected from the group consisting of SEQ ID NOS: 61 and 84, SEQ ID NOS: 62 and 87, SEQ ID NOS: 63 and 89, SEQ ID NOS: 64 and 84, SEQ ID NOS: 65 and 84, SEQ ID NOS: 66 and 85, and SEQ ID NOS: 67 and 88.

6. The purified preparation of claim 1 wherein the variable heavy chain CDR3 region and the variable light chain CDR3 region, respectively, are the amino acid sequence pairs selected from the group consisting of SEQ ID NOS: 61 and 86, SEQ ID NOS: 61 and 85, SEQ ID NOS: 61 and 87, SEQ ID NOS: 61 and 88, SEQ ID NOS: 61 and 89, SEQ ID NOS: 63 and 86, SEQ ID NOS: 63 and 85, SEQ ID NOS: 63 and 87, SEQ ID NOS: 63 and 88, and SEQ ID NOS: 63 and 84.

7. The purified preparation of claim 1 wherein the variable heavy chain CDR3 region and the variable light chain CDR3 region, respectively, are the amino acid sequence pairs selected from the group consisting of SEQ ID NOS: 71 and 87, SEQ ID NOS: 61 and 87, SEQ ID NOS: 72 and 87, SEQ ID NOS: 73 and 87, SEQ ID NOS: 74 and 87, SEQ ID NOS: 75 and 87, SEQ ID NOS: 76 and 87, SEQ ID NOS: 77 and 87, SEQ ID NOS: 78 and 87, SEQ ID NOS: 79 and 87, and SEQ ID NOS: 80 and 87.

8. The purified preparation of claim 1 wherein the variable heavy chain CDR3 region and the variable light chain CDR3 region, respectively, are the amino acid sequence pairs selected from the group consisting of SEQ ID NOS: 61 and 81, SEQ ID NOS: 69 and 81, and SEQ ID NOS: 70 and 81.

9. The purified preparation of claim 1, wherein the variable heavy chain CDR3 region, the variable light chain CDR3 region, and the variable heavy chain CDR1 region, respectively, are the amino acid sequences selected from the group consisting of SEQ ID NOS: 61, 86 and 48; SEQ ID NOS: 61, 86, and 49; SEQ ID NOS: 61, 86, and 50; SEQ ID NOS: 61, 86, and 51; SEQ ID NOS: 61, 86, and 52; SEQ ID NOS: 61, 86, and 53; SEQ ID NOS: 61, 86, and 54; SEQ ID NOS: 61, 86, and 55; SEQ ID NOS: 61, 86, and 56; SEQ ID NOS: 61, 86, and 57; SEQ ID NOS: 61, 86, and 82; and SEQ ID 61, 86, and 83.

10. A composition comprising a human antibody of claim 1 and a parmaceutically acceptable carrier.

* * * * *

```
                            SEQUENCE LISTING

<160> NUMBER OF SEQ ID NOS: 83

<210> SEQ ID NO 1
<211> LENGTH: 30
<212> TYPE: DNA
<213> ORGANISM: Homo sapiens

<400> SEQUENCE: 1
ggatttacct ttagcgagag ggccatgacc                                      30

<210> SEQ ID NO 2
<211> LENGTH: 30
<212> TYPE: DNA
<213> ORGANISM: Homo sapiens

<400> SEQUENCE: 2
ggatttacct ttagcgcggc catgatgacg                                      30

<210> SEQ ID NO 3
<211> LENGTH: 30
<212> TYPE: DNA
<213> ORGANISM: Homo sapiens

<400> SEQUENCE: 3
ggatttacct ttagcgggag catgatggcc                                      30

<210> SEQ ID NO 4
<211> LENGTH: 30
<212> TYPE: DNA
<213> ORGANISM: Homo sapiens

<400> SEQUENCE: 4
ggatttacct ttagcgactg ggcgatgacg                                      30

<210> SEQ ID NO 5
<211> LENGTH: 21
<212> TYPE: DNA
<213> ORGANISM: Homo sapiens

<400> SEQUENCE: 5
tctgctactc gttttgatta t                                               21
```

```
<210> SEQ ID NO 6
<211> LENGTH: 21
<212> TYPE: DNA
<213> ORGANISM: Homo sapiens

<400> SEQUENCE: 6
aatggtactc gtatggatgt t                                              21

<210> SEQ ID NO 7
<211> LENGTH: 24
<212> TYPE: DNA
<213> ORGANISM: Homo sapiens

<400> SEQUENCE: 7
ggtattgttc gtggtatgga tcat                                           24

<210> SEQ ID NO 8
<211> LENGTH: 21
<212> TYPE: DNA
<213> ORGANISM: Homo sapiens

<400> SEQUENCE: 8
ggtggttctc gttatgatgt t                                              21

<210> SEQ ID NO 9
<211> LENGTH: 21
<212> TYPE: DNA
<213> ORGANISM: Homo sapiens

<400> SEQUENCE: 9
aatattacta agtctgatgt t                                              21

<210> SEQ ID NO 10
<211> LENGTH: 21
<212> TYPE: DNA
<213> ORGANISM: Homo sapiens

<400> SEQUENCE: 10
ggtggtactc gttttgatta t                                              21

<210> SEQ ID NO 11
<211> LENGTH: 21
<212> TYPE: DNA
<213> ORGANISM: Homo sapiens

<400> SEQUENCE: 11
aatggtcgta atcttgatta t                                              21

<210> SEQ ID NO 12
<211> LENGTH: 21
<212> TYPE: DNA
<213> ORGANISM: Homo sapiens

<400> SEQUENCE: 12
actgctactc gttttgatta t                                              21

<210> SEQ ID NO 13
<211> LENGTH: 45
<212> TYPE: DNA
<213> ORGANISM: Homo sapiens

<400> SEQUENCE: 13
```

-continued aagccttttta ctggtaagta ttggggtcat actggttttg atatt                45

<210> SEQ ID NO 14
<211> LENGTH: 45
<212> TYPE: DNA
<213> ORGANISM: Homo sapiens

<400> SEQUENCE: 14 aaaccttttta ctggtaagta ttggggtcat actggttttg atatt                45

<210> SEQ ID NO 15
<211> LENGTH: 21
<212> TYPE: DNA
<213> ORGANISM: Homo sapiens

<400> SEQUENCE: 15
aatggcctgc gtatggatgt t                                           21

<210> SEQ ID NO 16
<211> LENGTH: 21
<212> TYPE: DNA
<213> ORGANISM: Homo sapiens

<400> SEQUENCE: 16
aatctgctgc gtatggatgt t                                           21

<210> SEQ ID NO 17
<211> LENGTH: 21
<212> TYPE: DNA
<213> ORGANISM: Homo sapiens

<400> SEQUENCE: 17
aatgcggtgc gtatggatgt t                                           21

<210> SEQ ID NO 18
<211> LENGTH: 21
<212> TYPE: DNA
<213> ORGANISM: Homo sapiens

<400> SEQUENCE: 18
aatgcgatgc gtatggatgt t                                           21

<210> SEQ ID NO 19
<211> LENGTH: 21
<212> TYPE: DNA
<213> ORGANISM: Homo sapiens

<400> SEQUENCE: 19
aatgccctcc gtatggatgt t                                           21

<210> SEQ ID NO 20
<211> LENGTH: 21
<212> TYPE: DNA
<213> ORGANISM: Homo sapiens

<400> SEQUENCE: 20
aatgtgctgc gtatggatgt t                                           21

<210> SEQ ID NO 21
<211> LENGTH: 21
<212> TYPE: DNA
<213> ORGANISM: Homo sapiens

<400> SEQUENCE: 21

```
gggggacgc gtatggatgt t                                              21

<210> SEQ ID NO 22
<211> LENGTH: 21
<212> TYPE: DNA
<213> ORGANISM: Homo sapiens

<400> SEQUENCE: 22
cagggcaccc gtatggatgt t                                             21

<210> SEQ ID NO 23
<211> LENGTH: 21
<212> TYPE: DNA
<213> ORGANISM: Homo sapiens

<400> SEQUENCE: 23
aatggcgtgc gtatggatgt t                                             21

<210> SEQ ID NO 24
<211> LENGTH: 21
<212> TYPE: DNA
<213> ORGANISM: Homo sapiens

<400> SEQUENCE: 24
aatggcatcc gtatggatgt t                                             21

<210> SEQ ID NO 25
<211> LENGTH: 42
<212> TYPE: DNA
<213> ORGANISM: Homo sapiens

<400> SEQUENCE: 25
acgggtacta gcagcgatag gacgcgcccg ccgaagtacg cc                      42

<210> SEQ ID NO 26
<211> LENGTH: 42
<212> TYPE: DNA
<213> ORGANISM: Homo sapiens

<400> SEQUENCE: 26
acgggtacta gcagcgatgt gtccggcctc aacatcgtgt cc                      42

<210> SEQ ID NO 27
<211> LENGTH: 30
<212> TYPE: DNA
<213> ORGANISM: Homo sapiens

<400> SEQUENCE: 27
cagagccgtg actatgagaa gcctatgatt                                    30

<210> SEQ ID NO 28
<211> LENGTH: 30
<212> TYPE: DNA
<213> ORGANISM: Homo sapiens

<400> SEQUENCE: 28
cagagccgag actatgagaa gcctatgatt                                    30

<210> SEQ ID NO 29
<211> LENGTH: 30
<212> TYPE: DNA
<213> ORGANISM: Homo sapiens
```

```
<400> SEQUENCE: 29
cagagccgcg actatgagaa gcctatgatt                                       30

<210> SEQ ID NO 30
<211> LENGTH: 30
<212> TYPE: DNA
<213> ORGANISM: Homo sapiens

<400> SEQUENCE: 30
cagagctatg accgtgcttt taagtctgtt                                       30

<210> SEQ ID NO 31
<211> LENGTH: 27
<212> TYPE: DNA
<213> ORGANISM: Homo sapiens

<400> SEQUENCE: 31
cagagctatg accataagaa gactgag                                          27

<210> SEQ ID NO 32
<211> LENGTH: 30
<212> TYPE: DNA
<213> ORGANISM: Homo sapiens

<400> SEQUENCE: 32
cagagctatg acatgtttgc tcgtgttatt                                       30

<210> SEQ ID NO 33
<211> LENGTH: 30
<212> TYPE: DNA
<213> ORGANISM: Homo sapiens

<400> SEQUENCE: 33
cagagctatg accgtctttta taagaagctt                                      30

<210> SEQ ID NO 34
<211> LENGTH: 30
<212> TYPE: DNA
<213> ORGANISM: Homo sapiens

<400> SEQUENCE: 34
cagagctatg accgggctta tcgacttctt                                       30

<210> SEQ ID NO 35
<211> LENGTH: 27
<212> TYPE: DNA
<213> ORGANISM: Homo sapiens

<400> SEQUENCE: 35
cagagctatg accgttctcg ttatgct                                          27

<210> SEQ ID NO 36
<211> LENGTH: 30
<212> TYPE: PRT
<213> ORGANISM: Homo sapiens

<400> SEQUENCE: 36

Gly Glu Glu Asp Leu Pro Ser Glu Glu Asp Ser Pro Arg Glu Glu Asp
 1               5                  10                  15

Pro Pro Gly Glu Glu Asp Leu Pro Gly Glu Glu Asp Leu Pro
            20                  25                  30
```

<210> SEQ ID NO 37
<211> LENGTH: 13
<212> TYPE: PRT
<213> ORGANISM: Homo sapiens

<400> SEQUENCE: 37

Pro Gly Glu Glu Asp Leu Pro Gly Glu Glu Asp Leu Pro
1               5                   10

<210> SEQ ID NO 38
<211> LENGTH: 12
<212> TYPE: PRT
<213> ORGANISM: Homo sapiens

<400> SEQUENCE: 38

Pro Ser Glu Glu Asp Ser Pro Arg Glu Glu Asp Pro
1               5                   10

<210> SEQ ID NO 39
<211> LENGTH: 7
<212> TYPE: PRT
<213> ORGANISM: Homo sapiens

<400> SEQUENCE: 39

Ser Ala Thr Arg Phe Asp Tyr
1               5

<210> SEQ ID NO 40
<211> LENGTH: 7
<212> TYPE: PRT
<213> ORGANISM: Homo sapiens

<400> SEQUENCE: 40

Asn Gly Thr Arg Met Asp Val
1               5

<210> SEQ ID NO 41
<211> LENGTH: 8
<212> TYPE: PRT
<213> ORGANISM: Homo sapiens

<400> SEQUENCE: 41

Gly Ile Val Arg Gly Met Asp His
1               5

<210> SEQ ID NO 42
<211> LENGTH: 7
<212> TYPE: PRT
<213> ORGANISM: Homo sapiens

<400> SEQUENCE: 42

Gly Gly Ser Arg Tyr Asp Val
1               5

<210> SEQ ID NO 43
<211> LENGTH: 7
<212> TYPE: PRT
<213> ORGANISM: Homo sapiens

<400> SEQUENCE: 43

Asn Ile Thr Lys Ser Asp Val
1               5

<210> SEQ ID NO 44
<211> LENGTH: 7

```
<212> TYPE: PRT
<213> ORGANISM: Homo sapiens

<400> SEQUENCE: 44

Gly Gly Thr Arg Phe Asp Tyr
1               5

<210> SEQ ID NO 45
<211> LENGTH: 7
<212> TYPE: PRT
<213> ORGANISM: Homo sapiens

<400> SEQUENCE: 45

Asn Gly Arg Asn Leu Asp Tyr
1               5

<210> SEQ ID NO 46
<211> LENGTH: 7
<212> TYPE: PRT
<213> ORGANISM: Homo sapiens

<400> SEQUENCE: 46

Thr Ala Thr Arg Phe Asp Tyr
1               5

<210> SEQ ID NO 47
<211> LENGTH: 15
<212> TYPE: PRT
<213> ORGANISM: Homo sapiens

<400> SEQUENCE: 47

Lys Pro Phe Thr Gly Lys Tyr Trp Gly His Thr Gly Phe Asp Ile
1               5                   10                  15

<210> SEQ ID NO 48
<211> LENGTH: 15
<212> TYPE: PRT
<213> ORGANISM: Homo sapiens

<400> SEQUENCE: 48

Lys Pro Phe Thr Gly Lys Tyr Trp Gly His Thr Gly Phe Asp Ile
1               5                   10                  15

<210> SEQ ID NO 49
<211> LENGTH: 7
<212> TYPE: PRT
<213> ORGANISM: Homo sapiens

<400> SEQUENCE: 49

Asn Gly Leu Arg Met Asp Val
1               5

<210> SEQ ID NO 50
<211> LENGTH: 7
<212> TYPE: PRT
<213> ORGANISM: Homo sapiens

<400> SEQUENCE: 50

Ser Ala Thr Arg Phe Asp Tyr
1               5

<210> SEQ ID NO 51
<211> LENGTH: 7
<212> TYPE: PRT
<213> ORGANISM: Homo sapiens
```

```
<400> SEQUENCE: 51

Asn Leu Leu Arg Met Asp Val
1               5

<210> SEQ ID NO 52
<211> LENGTH: 7
<212> TYPE: PRT
<213> ORGANISM: Homo sapiens

<400> SEQUENCE: 52

Asn Ala Val Arg Met Asp Val
1               5

<210> SEQ ID NO 53
<211> LENGTH: 7
<212> TYPE: PRT
<213> ORGANISM: Homo sapiens

<400> SEQUENCE: 53

Asn Ala Met Arg Met Asp Val
1               5

<210> SEQ ID NO 54
<211> LENGTH: 7
<212> TYPE: PRT
<213> ORGANISM: Homo sapiens

<400> SEQUENCE: 54

Asn Ala Leu Arg Met Asp Val
1               5

<210> SEQ ID NO 55
<211> LENGTH: 7
<212> TYPE: PRT
<213> ORGANISM: Homo sapiens

<400> SEQUENCE: 55

Asn Val Leu Arg Met Asp Val
1               5

<210> SEQ ID NO 56
<211> LENGTH: 7
<212> TYPE: PRT
<213> ORGANISM: Homo sapiens

<400> SEQUENCE: 56

Gly Gly Thr Arg Met Asp Val
1               5

<210> SEQ ID NO 57
<211> LENGTH: 7
<212> TYPE: PRT
<213> ORGANISM: Homo sapiens

<400> SEQUENCE: 57

Gln Gly Thr Arg Met Asp Val
1               5

<210> SEQ ID NO 58
<211> LENGTH: 7
<212> TYPE: PRT
<213> ORGANISM: Homo sapiens

<400> SEQUENCE: 58
```

```
Asn Gly Val Arg Met Asp Val
1               5

<210> SEQ ID NO 59
<211> LENGTH: 7
<212> TYPE: PRT
<213> ORGANISM: Homo sapiens

<400> SEQUENCE: 59

Asn Gly Ile Arg Met Asp Val
1               5

<210> SEQ ID NO 60
<211> LENGTH: 10
<212> TYPE: PRT
<213> ORGANISM: Homo sapiens

<400> SEQUENCE: 60

Gly Phe Thr Phe Ser Glu Arg Ala Met Thr
1               5                   10

<210> SEQ ID NO 61
<211> LENGTH: 10
<212> TYPE: PRT
<213> ORGANISM: Homo sapiens

<400> SEQUENCE: 61

Gly Phe Thr Phe Ser Ala Ala Met Met Thr
1               5                   10

<210> SEQ ID NO 62
<211> LENGTH: 10
<212> TYPE: PRT
<213> ORGANISM: Homo sapiens

<400> SEQUENCE: 62

Gly Phe Thr Phe Ser Gly Ser Met Met Ala
1               5                   10

<210> SEQ ID NO 63
<211> LENGTH: 10
<212> TYPE: PRT
<213> ORGANISM: Homo sapiens

<400> SEQUENCE: 63

Gly Phe Thr Phe Ser Asp Trp Ala Met Thr
1               5                   10

<210> SEQ ID NO 64
<211> LENGTH: 7
<212> TYPE: PRT
<213> ORGANISM: Homo sapiens

<400> SEQUENCE: 64

Ser Ala Thr Arg Phe Asp Tyr
1               5

<210> SEQ ID NO 65
<211> LENGTH: 10
<212> TYPE: PRT
<213> ORGANISM: Homo sapiens

<400> SEQUENCE: 65

Gln Ser Arg Asp Tyr Glu Lys Pro Met Ile
```

```
                1               5                   10
```

<210> SEQ ID NO 66
<211> LENGTH: 14
<212> TYPE: PRT
<213> ORGANISM: Homo sapiens

<400> SEQUENCE: 66

```
Thr Gly Thr Ser Ser Asp Arg Thr Arg Pro Pro Lys Tyr Ala
1               5                   10
```

<210> SEQ ID NO 67
<211> LENGTH: 14
<212> TYPE: PRT
<213> ORGANISM: Homo sapiens

<400> SEQUENCE: 67

```
Thr Gly Thr Ser Ser Asp Val Ser Gly Leu Asn Ile Val Ser
1               5                   10
```

<210> SEQ ID NO 68
<211> LENGTH: 10
<212> TYPE: PRT
<213> ORGANISM: Homo sapiens

<400> SEQUENCE: 68

```
Gln Ser Tyr Asp Arg Ala Phe Lys Ser Val
1               5                   10
```

<210> SEQ ID NO 69
<211> LENGTH: 9
<212> TYPE: PRT
<213> ORGANISM: Homo sapiens

<400> SEQUENCE: 69

```
Gln Ser Tyr Gly His Lys Lys Thr Glu
1               5
```

<210> SEQ ID NO 70
<211> LENGTH: 10
<212> TYPE: PRT
<213> ORGANISM: Homo sapiens

<400> SEQUENCE: 70

```
Gln Ser Tyr Asp Met Phe Ala Arg Val Ile
1               5                   10
```

<210> SEQ ID NO 71
<211> LENGTH: 10
<212> TYPE: PRT
<213> ORGANISM: Homo sapiens

<400> SEQUENCE: 71

```
Gln Ser Tyr Asp Arg Leu Tyr Lys Lys Leu
1               5                   10
```

<210> SEQ ID NO 72
<211> LENGTH: 10
<212> TYPE: PRT
<213> ORGANISM: Homo sapiens

<400> SEQUENCE: 72

```
Gln Ser Tyr Asp Arg Ala Tyr Arg Leu Leu
1               5                   10
```

```
<210> SEQ ID NO 73
<211> LENGTH: 9
<212> TYPE: PRT
<213> ORGANISM: Homo sapiens

<400> SEQUENCE: 73

Gln Ser Tyr Asp Arg Ser Arg Tyr Ala
1               5

<210> SEQ ID NO 74
<211> LENGTH: 30
<212> TYPE: DNA
<213> ORGANISM: Homo sapiens

<400> SEQUENCE: 74
ggatttacct ttagcagcta tgcgatgagc                                30

<210> SEQ ID NO 75
<211> LENGTH: 30
<212> TYPE: DNA
<213> ORGANISM: Homo sapiens

<400> SEQUENCE: 75
ggatttacct ttgtgaagag catggtggtg                                30

<210> SEQ ID NO 76
<211> LENGTH: 30
<212> TYPE: DNA
<213> ORGANISM: Homo sapiens

<400> SEQUENCE: 76
ggatttacct ttagcaggaa cctgatgacc                                30

<210> SEQ ID NO 77
<211> LENGTH: 30
<212> TYPE: DNA
<213> ORGANISM: Homo sapiens

<400> SEQUENCE: 77
ggatttacct ttgagcggtg gatgggggcg                                30

<210> SEQ ID NO 78
<211> LENGTH: 30
<212> TYPE: DNA
<213> ORGANISM: Homo sapiens

<400> SEQUENCE: 78
ggatttacct ttagcaggag gatgatggtc                                30

<210> SEQ ID NO 79
<211> LENGTH: 30
<212> TYPE: DNA
<213> ORGANISM: Homo sapiens

<400> SEQUENCE: 79
ggatttacct ttagcaggtg gatgatggtc                                30

<210> SEQ ID NO 80
<211> LENGTH: 30
<212> TYPE: DNA
<213> ORGANISM: Homo sapiens

<400> SEQUENCE: 80
```

-continued

```
ggatttacct ttagcgagag catgatgacg                                30

<210> SEQ ID NO 81
<211> LENGTH: 30
<212> TYPE: DNA
<213> ORGANISM: Homo sapiens

<400> SEQUENCE: 81
ggatttacct ttagctggca catgatgacg                                30

<210> SEQ ID NO 82
<211> LENGTH: 30
<212> TYPE: DNA
<213> ORGANISM: Homo sapiens

<400> SEQUENCE: 82
ggatttacct ttagctccgt gatgatgacg                                30

<210> SEQ ID NO 83
<211> LENGTH: 30
<212> TYPE: DNA
<213> ORGANISM: Homo sapiens

<400> SEQUENCE: 83
ggatttacct ttagcgggag catgatgacg                                30
```